US00PP27525P3

(12) United States Plant Patent
Boekestijn

(10) Patent No.: US PP27,525 P3
(45) Date of Patent: Jan. 3, 2017

(54) ***CAPSICUM ANNUUM* PLANT NAMED 'BOEKTASPEP2'**

(50) Latin Name: *Capsicum annuum*
Varietal Denomination: BOEKTASPEP2

(71) Applicant: Westland Peppers Innovation BV, De Lier (NL)

(72) Inventor: Pieter Boekestijn, De Lier (NL)

( * ) Notice: Subject to any disclaimer, the term of this patent is extended or adjusted under 35 U.S.C. 154(b) by 114 days.

(21) Appl. No.: 14/544,202

(22) Filed: Dec. 9, 2014

(65) Prior Publication Data

US 2016/0165781 P1 Jun. 9, 2016

(51) Int. Cl.
*A01H 5/08* (2006.01)

(52) U.S. Cl.
USPC ..... Plt./258

(58) Field of Classification Search
USPC ..... Plt./258, 263.1
See application file for complete search history.

(56) References Cited

PUBLICATIONS

Fresh Plaza Netherlands: Westland Peppers introduces new seedless mini peppers, retrieved on May 19, 2016, retrieved from the Internet at <http://www.freshplaza.com/article/110816/Netherlands-Westland-Peppers-introduces-seedless-mini-peppers> 3 pp.*

European Union Trademark Tasty Pep retrieved on May 19, 2016, retrieved from the Internet at <https://tmdb.eu/trademark/010727626/eu> 6 pp.*

* cited by examiner

*Primary Examiner* — June Hwu
(74) *Attorney, Agent, or Firm* — Samuel R. McCoy, Jr.

(57) ABSTRACT

'BOEKTASPEP2' is a distinctive variety of *Capsicum annuum* which is characterized by the combination of seedless of near-seedless fruit, a high percentage of fruit possessing no seeds, a large fruit size, fruit with a sweet taste, fruit with a vivid orange color, a unique shape of the fruit, as well as the stability and uniformity of traits through successive cycles of asexual propagation.

5 Drawing Sheets

Latin name of the genus and species: The Latin name of the genus and species of the novel variety disclosed herein is *Capsicum annuum.*

Variety denomination: The inventive variety of *Capsicum annuum* disclosed herein has been given the variety denomination 'BOEKTASPEP2'.

BACKGROUND OF THE INVENTION

The present invention relates to a new and distinct cultivar of *Capsicum annuum*, commonly called bell pepper, which has been given the variety denomination of 'BOEKTASPEP2'. Its market class is PLT/258.

Parentage: The *Capsicum annuum* variety 'BOEKTASPEP2' originated as a naturally occurring, whole plant mutation of *Capsicum annuum* 'Jaydee' (unpatented in the United States, NL Plant Breeder's Rights No. 34730, and QZ Plant Breeder's Rights No. 34162 which was subsequently surrendered), a variety developed and owned by the inventor.

The inventor of 'BOEKTASPEP2' is a commercial bell pepper producer in De Lier, The Netherlands and frequently observes whole plant mutations of *Capsicum annuum* 'Jaydee' at his commercial greenhouse operation. For said mutations which seem to exhibit commercial potential, cuttings are taken to produce trial plants which are subsequently grown for evaluation. At the time of the initial selection, all relevant characteristics are observed and compared with both current commercial varieties as well as with other selections. In October of each year, a determination is made with respect to each candidate variety to determine if there is enough commercial potential to continue with evaluations. Some candidates are discarded. For those candidate varieties that are not discarded, additional cuttings are taken to produce trial plants for a second year of evaluation for commercial potential. After the second year, a final determination is made with respect to each candidate variety.

The variety now called 'BOEKTASPEP2' was initially discovered in April 2012. At that time, cuttings were taken and the resulting plants were evaluated at the inventor's greenhouse until October of 2012. At that time it was determined that said variety exhibited certain distinguishing characteristics that would prove favorable for commercial production and marketability. Consequently, the candidate variety was selected for a second year of evaluations, which proceeded from late in 2013 until October of 2014, after which time a final determination was made as to the candidate variety's commercial potential. The candidate variety was given the breeder denomination 'BOEKTASPEP2'.

Asexual Reproduction: 'BOEKTASPEP2' was first asexually propagated by softwood stem cuttings in April of 2012 at a greenhouse in De Lier, The Netherlands under the control of the inventor and has since been vegetatively propagated through one additional generation. The distinctive characteristics of the inventive 'BOEKTASPEP2' variety are stable from generation to generation; clones of the variety produced by asexual reproduction maintain the distinguishing characteristics of the original plant.

SUMMARY OF THE INVENTION

The following characteristics have been repeatedly observed and represent the distinguishing characteristics of the new *Capsicum* cultivar 'BOEKTASPEP2'. These traits in combination distinguish 'BOEKTASPEP2' as a new and distinct cultivar.

1. *Capsicum* 'BOEKTASPEP2' exhibits seedless or near-seedless fruit.
2. *Capsicum* 'BOEKTASPEP2' exhibits a high percentage of seedless fruit.
3. *Capsicum* 'BOEKTASPEP2' exhibits fruit with a notably long shelf life.
4. *Capsicum* 'BOEKTASPEP2' exhibits fruit with a notably sweet taste.
5. *Capsicum* 'BOEKTASPEP2' exhibits fruit with a vivid orange color.
6. *Capsicum* 'BOEKTASPEP2' exhibits fruit with two locules and, as a result, a latitudinal cross-section in the general shape of the figure "eight".
7. *Capsicum* 'BOEKTASPEP2' exhibits a large fruit size.

BOTANICAL DESCRIPTION OF THE PLANT

Figure 1:
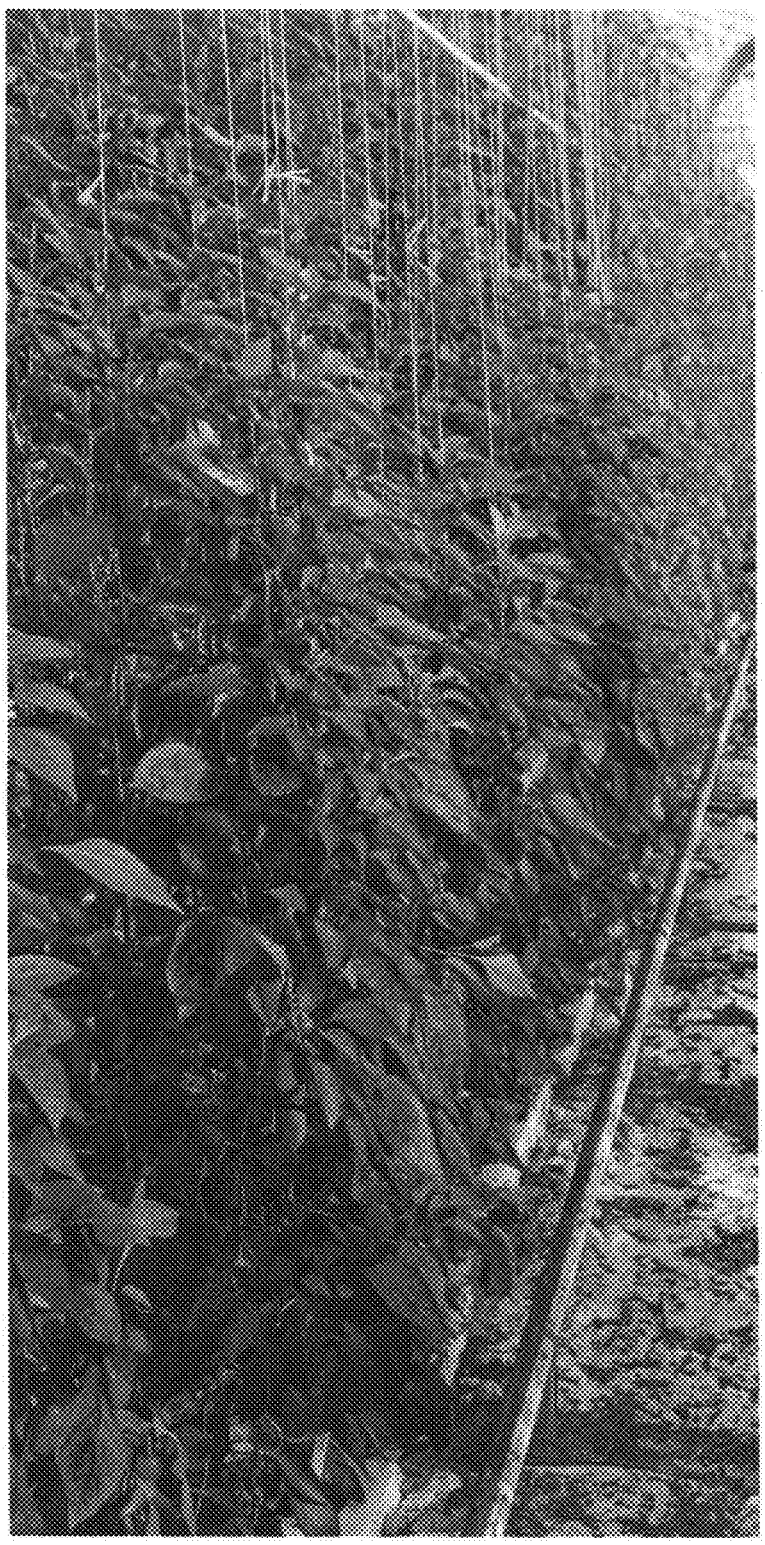
FIG. 1 shows, as nearly true as it is reasonably possible to make the same in color illustrations of this type, an exemplary specimens of the new cultivar, 'BOEKTASPEP2'. The plants shown are approximately 4 months old and were grown in a climate-controlled greenhouse in De Lier, The Netherlands.
Figure 2:
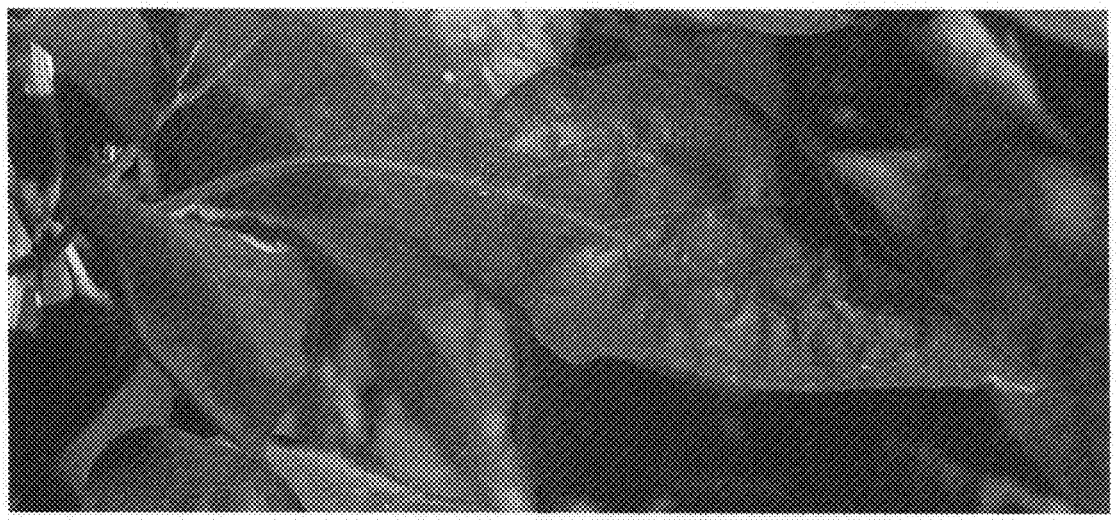
FIG. 2 shows, as nearly true as it is reasonably possible to make the same in color illustrations of this type, the foliage of 'BOEKTASPEP2'.
Figure 3:
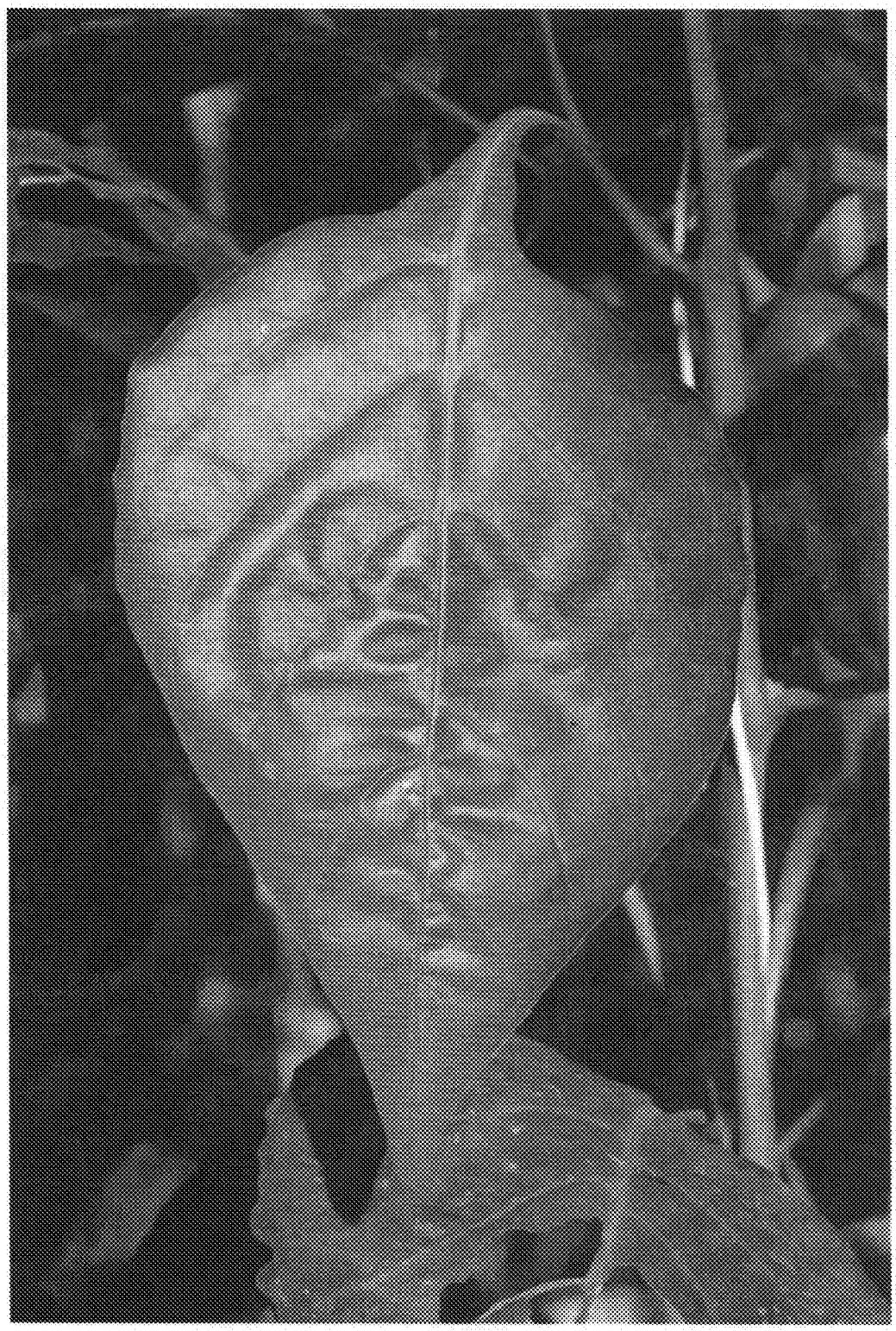
FIG. 3 shows, as nearly true as it is reasonably possible to make the same in color illustrations of this type, the foliage of 'BOEKTASPEP2'.
Figure 4:
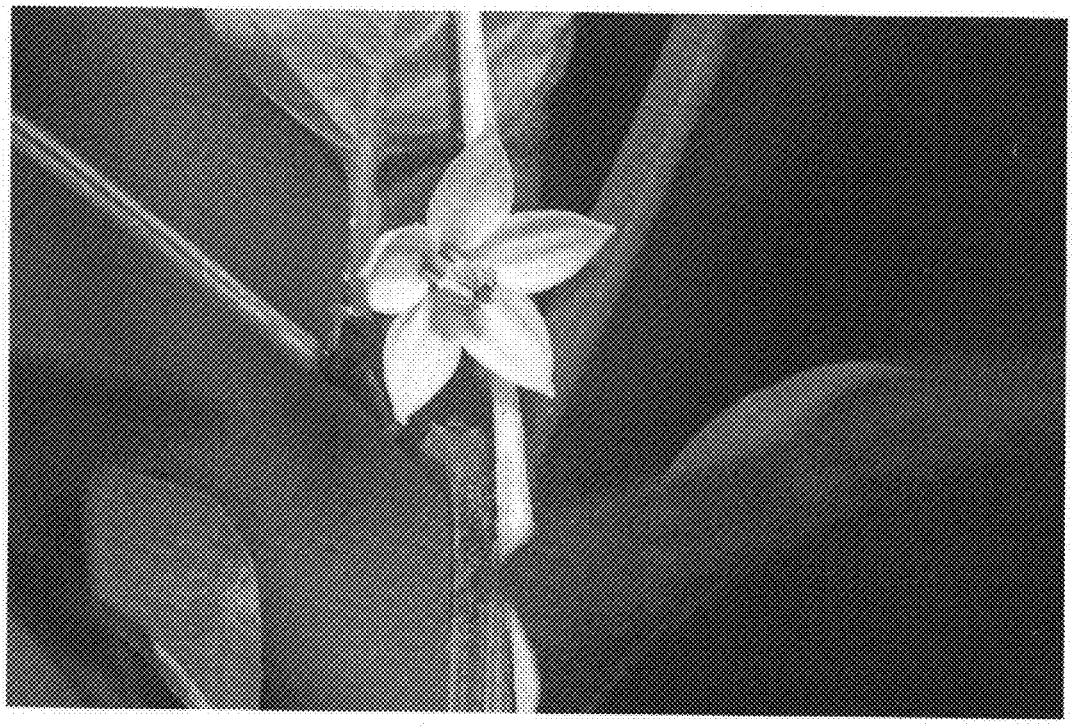
FIG. 4 shows, as nearly true as it is reasonably possible to make the same in color illustrations of this type, the flower of 'BOEKTASPEP2'.
Figure 5:
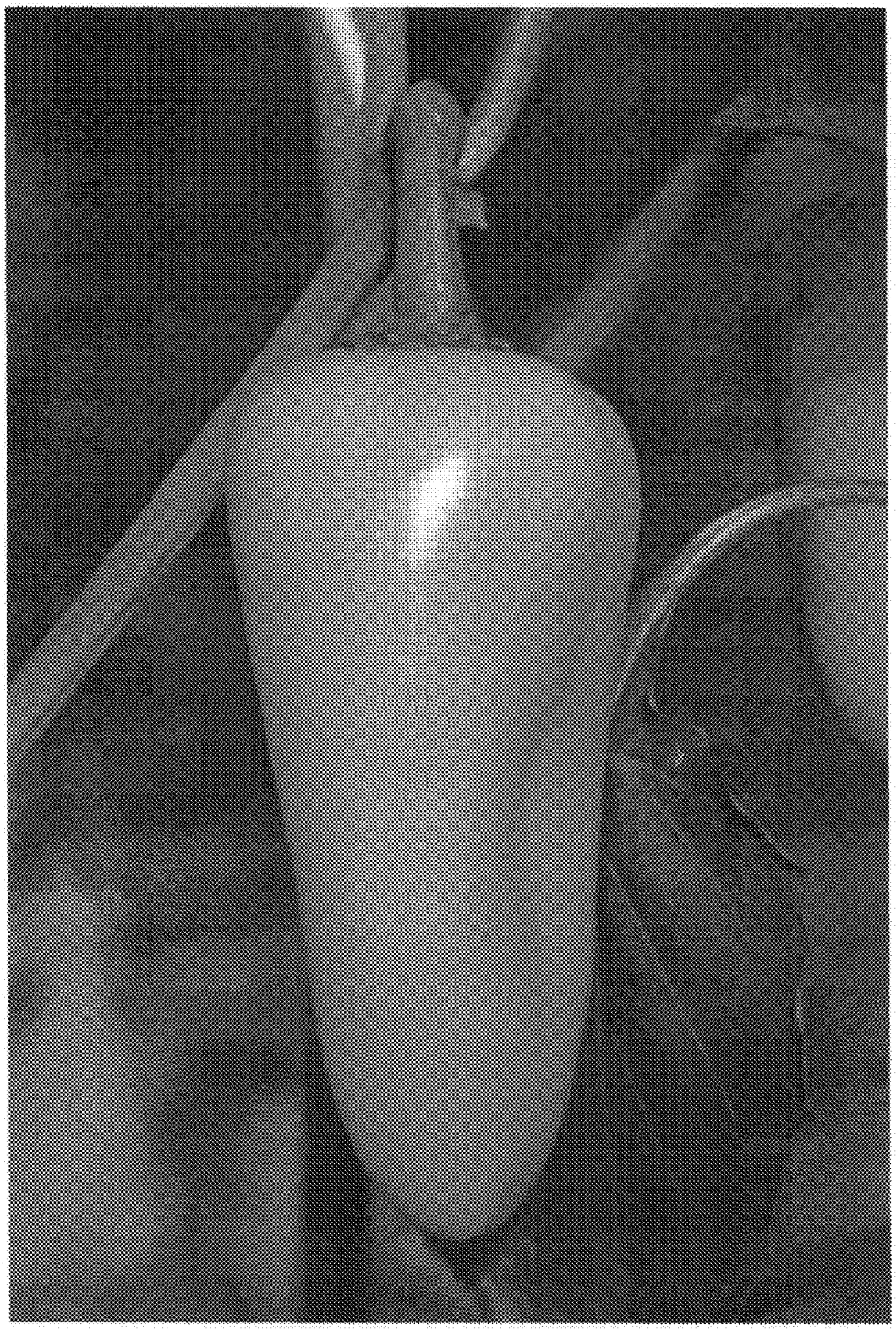
FIG. 5 shows, as nearly true as it is reasonably possible to make the same in color illustrations of this type, the fruit of 'BOEKTASPEP2'.

The following is a detailed botanical description of a new and distinct variety of *Capsicum annuum* known as 'BOEKTASPEP2', based upon observations of plants, approximately 4 months old from a rooted cutting, grown in a climate-controlled greenhouse in De Lier, The Netherlands. Temperatures ranged from 28 degrees Celsius during the day and 12 degrees Celsius at night. No artificial light, photoperiodic treatments or chemical treatments were given to the plants. Observation data was recorded in November of 2014.

Those skilled in the art will appreciate that certain characteristics will vary with older or, conversely, with younger plants. 'BOEKTASPEP2' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climactic and cultural conditions. Color notations are based on *The Royal Horticultural Society Colour Chart*, The Royal Horticultural Society, London, 2007 edition.

A botanical description of 'BOEKTASPEP2' and comparisons with other varieties of *Capsicum annuum* are provided below.

Technical Description of the Variety

Plant description:

- *Growth rate*.—Moderate; approximately 30 cm per month during the growing season.
- *Growth habit*.—Upright, trailing.
- *Height*.—167.5 cm in height.
- *Width*.—55.0 cm in width.
- *Cold hardiness*.—Tolerates temperatures from approximately 2 degrees Celsius to, at least, 40 degrees Celsius.
- *Propagation*.—Nodal cuttings and grafting.
- *Time to initiate roots*.—Approximately 7 to 14 days to initiate roots at 20° Centigrade.
- *Time to produce a rooted cutting*.—Approximately 21 days to produce a rooted cutting.
- *Disease and pest resistance*.—Neither tolerance nor resistance to normal diseases and pests of *Capsicum annuum* have been observed.
- *Drought resistance*.—Plants can survive for at least 2 weeks without supplemental water without a change in foliage color, or detrimental effects to the plant.

Root system: Fibrous.

Stem:

- *Number of leaves per stem*.—Approximately 20.
- *Stem cross-section*.—Slightly to moderately quadrangulate.
- *Stem length*.—Approximately 161.0 cm.
- *Stem width*.—Approximately 0.8 cm.
- *Stem color*.—Green to yellow-green; near RHS 143A and 144A to 144B.
- *Stem texture*.—Glabrous; matte.

Foliage:

- *Leaf arrangement*.—Alternate.
- *Quantity of leaves per plant*.—Approximately 160.
- *Leaf shape*.—Ovate.
- *Leaf apex*.—Apiculate.
- *Leaf base*.—Acuminate.
- *Leaf length*.—Average of 18.3 cm in length.
- *Leaf width*.—Average of 8.8 cm in width.
- *Texture* (*adaxial surface*).—Glabrous; moderately glossy.
- *Texture* (*abaxial surface*).—Glabrous except for main vein; moderately glossy.
- *Pubescence* (*adaxial surface*).—Absent.
- *Pubescence* (*abaxial surface*).—Absent, except for main vein; sparsely to moderately covered with very short soft hairs, approximately 0.75 mm long and colored green-white; near RHS 157D.
- *Leaf margin*.—Entire, very slightly undulate, slightly concave and involute.
- *Young leaf color* (*adaxial surface*).—Green; near RHS 143A.
- *Young leaf color* (*abaxial surface*).—Yellow-green; near RHS 144A.
- *Mature leaf color* (*adaxial surface*).—Green; near RHS N137A.
- *Mature leaf color* (*abaxial surface*).—Yellow-green; in between near RHS 146B and 147B, closest to 147B.
- *Venation*.—Pinnate.

*Vein color* (*adaxial surface*).—Yellow-green; near RHS 144B.

*Vein color* (*abaxial surface*).—Yellow-green; near RHS 148D.

*Petiole*.—Glabrous and slightly glossy; approximately 81 mm long and 4 mm wide; colored green to yellow-green, near RHS 143A and 144A to 144B.

Bud:

*Flower bud shape*.—Obovate, top flattened, nodding.

*Flower bud length*.—7 mm in length, at approximately 5 days prior to opening.

*Flower bud diameter*.—5 mm in diameter, at approximately 5 days prior to opening.

*Bud color*.—Green-white; near RHS 157B and 157C.

Inflorescence and flower:

*Inflorescence*.—None; flowers are solitary.

*Flowering arrangement*.—Solitary; axillary; pedicellate.

*Natural flowering season*.—Approximately 60 to 80 days after planting.

*Rate of flower opening*.—Approximately 10 days from bud-forming to fully opened flower.

*Flower longevity on plant*.—Approximately 4 days.

*Fragrance*.—Absent.

*Pedicels*.—Length — Approximately 8 mm. Width — Approximately 1.5 mm. Aspect — Approximate angle to stem: 45°, curved downward in an approximate angle of 45° to vertical. Color — Green; near RHS 143B.

*Perianth*.—Individual Flowers; Corolla — Arrangement rotate; approximate diameter of corolla: 2.0 cm, approximate depth of corolla: 12 mm. Petal Description — Quantity — Average: 5, occasionally 6. Length — Approximately 12 mm. Width — Approximately 8 mm at widest point. Margin — Entire. Shape — Elliptic. Apex — Apiculate to acute. Base — Cuneate, lower 25% fused. Texture — Glabrous, slightly glossy, moderately velvety. Color — Immature: White; near RHS 155A. Fully Opened Interior — White; near RHS 155B. Fully Opened Exterior — White; near RHS 155B. Fading — White to yellow-white; in between near RHS 155A and 158D.

*Calyx*.—Calyx Arrangement — Fused into a campanulate shape. Sepals — Sepal Appearance — Glossy and smooth. Sepal Arrangement — Paired, placed at both sides of the corolla. Quantity — Two in number. Sepal Shape — Lanceolate, involute. Sepal Margin — Entire. Sepal Apex — Acute. Sepal Base — Cuneate. Sepal Length — Average 26 mm. Sepal Width — Average 4 mm. Immature Sepal Color (adaxial surface) — 145C, margins 63B. Immature Sepal Color (abaxial surface) — 145C, margins 63B. Mature Sepal Color (adaxial surface) — 145C, margins 63C. Mature Sepal Color (abaxial surface) — 145C, margins 63C.

Reproductive organs:

*Stamens*.—Number — Average of 5. Filament Length — Approximately 3 mm. Filament Color — White; near RHS 155A. Anther Length — Approximately 2 mm. Anther Color — Violet-blue; near RHS 98c to 98D. Anther Shape — Narrow ovate to near oblong. Pollen — Moderate to high. Pollen Color — White; near RHS 155B to 155C.

*Pistil*.—Pistil number — Average of 1. Pistil length, Including Style — Approximately 3 mm. Stigma shape — Club-shaped. Stigma color — Yellow-green; near RHS 150A to 150B. Style length — Approximately 2.75 mm. Style color — Yellow-green; near RHS 150D. Ovary Position — Superior. Ovary color — Yellow-green; near RHS N144C.

Seed and fruit:

*Fruit*.—Type — Berry. Time to reach maturity — Early. General Shape — Longitudinal Cross-section — Tapered bell shape; ovate to narrow oblong. Latitudinal Cross-section — Oblong and generally in the shape of the figure "eight"; two locules. Shape of Apex — Retuse. Stalk Cavity — Absent. Stalk Cavity Depth — Not Applicable; stalk cavity absent. Depth of Interloculary Grooves — Average of 1.5 mm (varying between 0 and 2 mm). Attitude — Drooping. Color, immature fruit — Green, in between RHS 140B and RHS 140C. Color, mature fruit — Orange; near RHS N25A. Texture — Glabrous, glossy, very smooth. Dimensions — Approximately 79 mm long and 39 mm wide. Length-to-Width Ratio — Approximately 1:0.49. Thickness of Flesh — Approximately 5.5 mm at maturity. Calyx aspect — Non-enveloping. Number of days fruit can be stored — 14 days at 13 degrees Celsius.

*Seed*.—Presence/Amount — Seed is normally not produced. Only under special circumstances, as in the presence of an overabundance of pollinators in the immediate vicinity of the plant, is a negligible amount of seed sporadically observed in some of the present fruit. Amount of Seed When Present — Approximately 28 per fruit. Shape — Disc-like. Dimensions — Average diameter is 4 mm, and the average width at the narrowest point is 1 mm. Texture — Glabrous, slightly velvety. Color — Yellow-white; near RHS 158D.

Comparisons With The Parent

Plants of the new cultivar 'BOEKTASPEP2' are comparable to the parent variety *Capsicum annuum* 'Jaydee' (unpatented) in that both varieties exhibit orange fruit when mature and both cultivars are said to produce seedless or near-seedless fruit. However, 'BOEKTASPEP2' exhibits a higher percentage of fruit producing no seeds when compared to 'Jaydee'. Also, the fruit of 'BOEKTASPEP2' possesses only two locules, producing a latitudinal cross-section shape that is generally in the shape of the figure "eight", whereas 'Jaydee' possesses four locules creating a trapezoidal-shaped latitudinal cross-section. 'BOEKTASPEP2' also exhibits larger flowers, a darker green foliage color and more plant vigor when compared to 'Jaydee'.

Comparison With The Most Similar Cultivar Known To The Inventor

Plants of the new cultivar 'BOEKTASPEP2' are comparable to the cultivar *Capsicum* 'Angello' (unpatented). A comparison of 'BOEKTASPEP2' with 'Angello' is described in Chart 1.

CHART 1

| Characteristic | 'BOEKTASPEP2' | 'Angello' |
|---|---|---|
| Length of internodes. | Longer. | Shorter. |
| Fruit; longitudinal cross-section. | Tapered bell shape; ovate to narrow oblong and relatively short. | Narrow oblong and relatively long. |
| Fruit; immature color. | Green, RHS 140B and 140C. | Green, RHS 135C. |
| Fruit; mature color. | Orange, RHS N25A. | Yellow-orange, RHS 18A to 19A. |
| Fruit; sweetness. | Sweeter than 'Angello'. | Less sweet than 'BOEKTASPEP2'. |

CHART 1-continued

| Characteristic | 'BOEKTASPEP2' | 'Angello' |
|---|---|---|
| Fruit; aroma. | Less sour than 'Angello'. | More sour than 'BOEKTASPEP2'. |

That which is claimed is:

1. A new and distinct variety of *Capsicum annuum* plant named 'BOEKTASPEP2', substantially as described and illustrated herein.

* * * * *